(12) United States Patent
Paganelli

(10) Patent No.: US 6,767,127 B2
(45) Date of Patent: Jul. 27, 2004

(54) OPTICAL DILATOMETER

(75) Inventor: Mariano Paganelli, Modena (IT)

(73) Assignee: Expert System Solutions S.R.L., Modena (IT)

( * ) Notice: Subject to any disclaimer, the term of this patent is extended or adjusted under 35 U.S.C. 154(b) by 83 days.

(21) Appl. No.: 10/293,342

(22) Filed: Nov. 14, 2002

(65) Prior Publication Data

US 2003/0108082 A1 Jun. 12, 2003

(30) Foreign Application Priority Data

Dec. 12, 2001 (IT) .................................. MO2001A0248

(51) Int. Cl.[7] ........................ G01N 25/00; G01B 11/04; G01B 11/02
(52) U.S. Cl. ........................ 374/55; 356/634; 356/625
(58) Field of Search ..................... 374/55, 187, 195; 356/634, 625

(56) References Cited

U.S. PATENT DOCUMENTS

| | | | | |
|---|---|---|---|---|
| 3,788,746 A | * | 1/1974 | Baldwin et al. ............ | 356/485 |
| 4,636,969 A | * | 1/1987 | Kyoden et al. ............. | 702/155 |
| 4,762,424 A | * | 8/1988 | Baricevac et al. .......... | 374/56 |
| 4,924,477 A | * | 5/1990 | Gilmore et al. ............ | 374/55 |
| 4,930,894 A | * | 6/1990 | Baldwin .................... | 356/485 |
| 5,231,285 A | * | 7/1993 | Berg ........................ | 250/231.1 |
| 5,479,261 A | * | 12/1995 | Hansen ...................... | 356/628 |
| 6,400,449 B2 | * | 6/2002 | Maris et al. ................ | 356/72 |
| 6,476,922 B2 | * | 11/2002 | Paganelli .................... | 356/634 |

FOREIGN PATENT DOCUMENTS

DE          3514000 A1 * 10/1986  .......... G01N/25/16

* cited by examiner

Primary Examiner—Gail Verbitsky
Assistant Examiner—V Brown
(74) Attorney, Agent, or Firm—Browdy and Neimark, P.L.L.C.

(57) ABSTRACT

The invention comprises: a rest base (1) for a sample (2) to be examined, at least a first and a second optical systems (3, 4), identifying two optical paths located at a predetermined distance one from another. The at least a first and a second optical systems (3, 4) are commandable and are able to focus, with a predetermined enlargement, on two ends of the sample (2). The at least a first and a second optical systems (3, 4) are arranged and maintained on parallel planes which are also parallel to the rest base (1). The invention also comprises at least a monitoring and measuring device able to gather images sent by the at least a first and a second optical systems (3, 4). The apparatus is structured to carry out measurements of dimensions of a sample (2) while completely eliminating any influence on the measurements by the measuring system and the rest base for the sample.

7 Claims, 3 Drawing Sheets

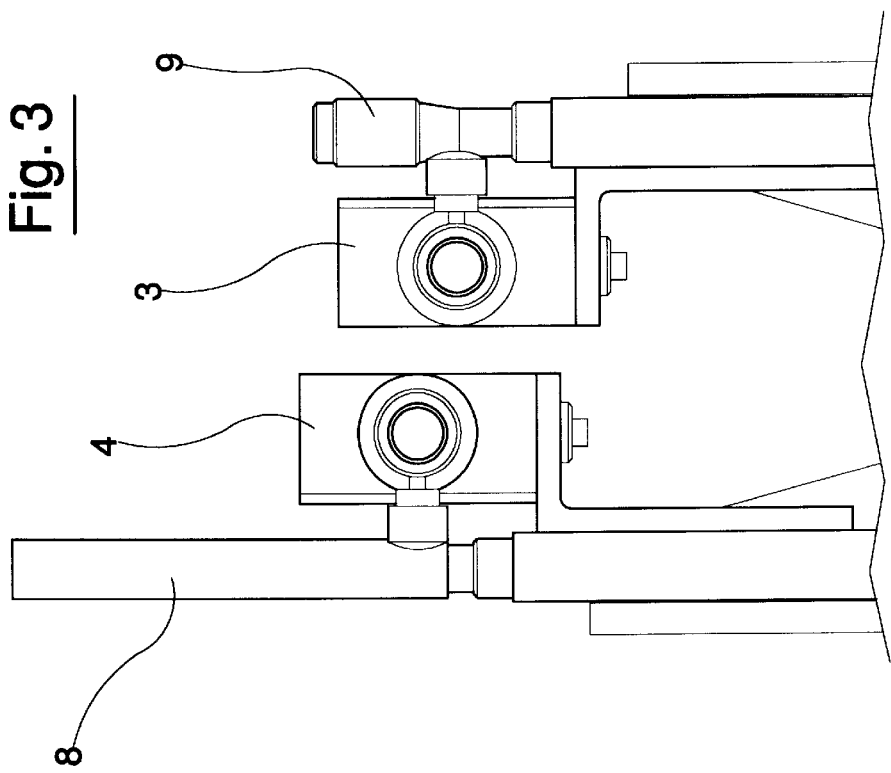
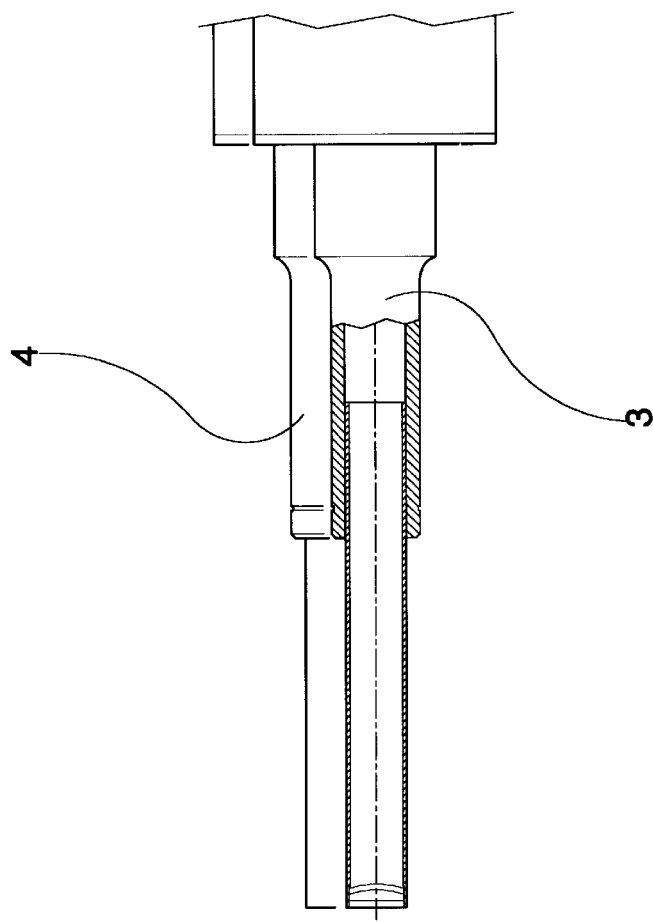

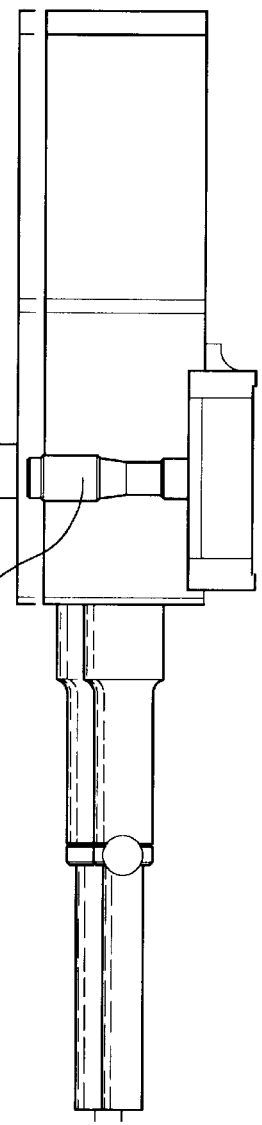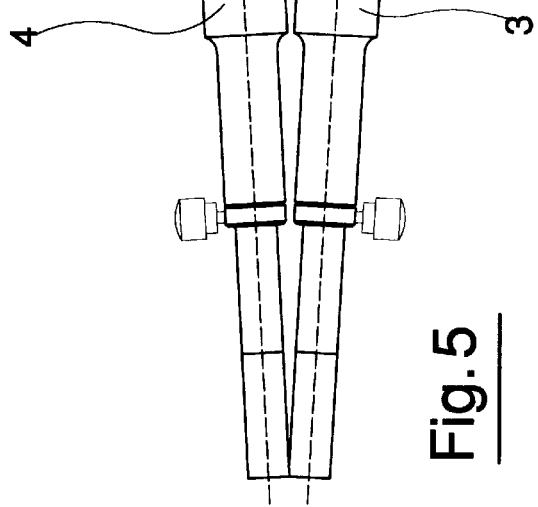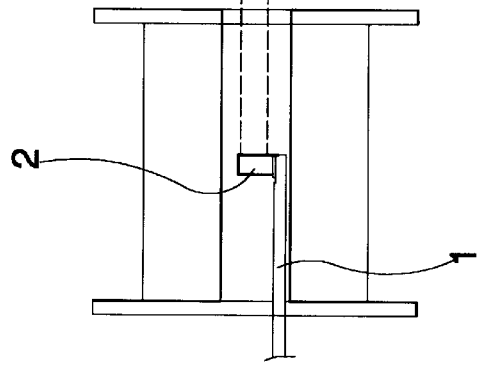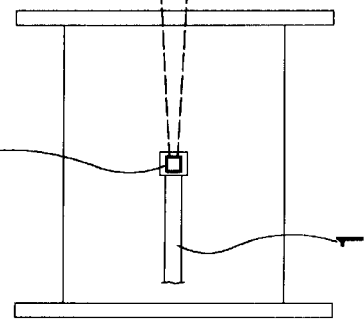

OPTICAL DILATOMETER

BACKGROUND OF THE INVENTION

The task of a dilatometer is to measure the linear dimensional variation of a sample upon a variation in the temperature to which the sample is exposed. The sample is placed inside a generally tubular oven, and the temperature in the oven is controlled and varied. The dimensional variations of the sample on temperature variation are read by instruments known as dilatometers, which can differ from each other in terms of the system used for heating the sample and also in terms of the system for measuring the dimensional variations. The dimensional measuring methods are mechanical, electronic or optical, while the heating systems are almost always electrical, by radiation.

In mechanical dilatometers the sample is materially in contact with a system of levers which amplify each tiny variation in size, and record the variation on a sheet of paper by means of a pen.

In electronic dilatometers the sample is in contact with a small rod made of refractory material which transfers the dimensional variations to an electrical device through a differential transformer. The electric signal is then amplified and transformed into a graph using a recording system.

The optical dilatometer measures the dimensional variations by means of a ray of light which is deflected from a small mirror connected by a lever to the sample being measured.

With a laser beam it is possible to carry out the measuring operation using the Abbe method (optical interferometry), which reaches a resolution which is equal to the wave length of the light used.

A recent innovation in the field of dilatometry is the chance to carry out the measurement of the dimensional variations without touching the sample, but simply by observing it with a high-definition camera. In this way measures can be made of samples in a semi-liquid or even liquid state.

In the majority of cases the sample inside the oven is in contact with a measuring system that is inevitably subject to deformations which influence the accuracy of the measurement and, in all cases, is in contact with a support which, as it is prone to substantial dimensional variations during the measuring operation, must have an effect on the results of the operation.

It is therefore always necessary to carry out a calibration of the instrument which is done by performing a measuring operation of a sample which has a known dilatation in order that the deviations from the zero line produced by the dilation of the instrument itself can be calculated.

In the case of mechanical or electronic dilatometers, where the sample is located in a sample-holder made of refractory material and the dimensional variations are read by a rod made of refractory material, the situation created is rather complex, in that all of the elements of the measuring system are subject to thermal dilations. The result of this complex sum of different dilations can be that the dilation of the measuring system is of the same order as the dilation of the sample under examination. Naturally the dilation of the measuring system must be subtracted from the dilation of the sample, an operation that can be done manually or automatically. These system calibrating operations must be frequently repeated since as the materials age their thermomechanical properties change; a standard control procedure is necessary, at predetermined intervals.

Often a same material gives different dilation data if measured using different instruments, due to the fact that the calibration procedure has not been carried out in the same way as before.

Even for optical dilatometers where there is no contact, the instrument calibration problem persists, in that even though the sample is not touched by the measuring system it still has to be supported in order to guarantee a perfect positioning thereof inside the oven chamber. This support too is subject to thermal dilations which have to be measure and subtracted from the dilations of the sample during the course of the examination.

All of the above leads to considerable doubt over the exactness of the measurements, and extreme caution when taking the measurements.

A recent optical dilatometer, described by the same applicant, solves the problems connected with the dilation of the measuring system and/or the sample support method, virtually eliminating the tedious task of calculating a calibration curve; it further enables dynamic dilatometric measurements to be made, i.e. measurements in which the sample under examination is subjected to continuously-variable temperatures.

The above-mentioned recent dilatometer, which was described in a patent belonging to the present applicant, comprises a rest base for the sample and two optical systems which identify two optical paths, parallel to and aligned with the rest base, the paths being located at a predetermined distance from each other and being able to focus the images of the ends of the sample being measured. The dilatometer further comprises a visualising and measuring device which can gather the images focussed-upon by the optical systems. This dilatometer is very precise and impervious to the measuring system dilations, but can carry out measurements through only a rather limited interval of variation, in that the optical paths cannot follow and focus on large dilations; this makes the dilatometer unsuitable for measuring materials which have a high coefficient of dilation, or for measuring samples subjected to large-range thermal gradients.

The main aim of the present invention is to obviate the limitations and lacks in the prior art.

An advantage of the invention is that it maintains a high measuring precision, is not influenced by the dilations of the measuring system, and is able to operate in an extremely wide dilation interval—much wider than any range measurable by existing dilatometers of the same type.

These aims and more besides are all attained by the invention as it is characterised in the claims that follow.

SUMMARY OF THE INVENTION

The invention comprises: a rest base for a sample to be examined, at least a first and a second optical systems, identifying two optical paths located at a predetermined distance one from another. The at least a first and a second optical systems are commandable and are able to focus, with a predetermined enlargement, on two ends of the sample. The at least a first and a second optical systems are arranged and maintained on parallel planes which are also parallel to the rest base. The invention also comprises at least a monitoring and measuring device able to gather images sent by the at least a first and a second optical systems. The apparatus is structured to carry out measurements of dimensions of a sample while completely eliminating any influence on the measurements by the measuring system and the rest base for the sample.

BRIEF DESCRIPTION OF THE DRAWINGS

Further characteristics and advantages of the present invention will better emerge from the detailed description that follows, of a preferred but nonexclusive embodiment of the invention, illustrated purely by way of example in the appended figures of the drawings, in which:

FIG. 2 is a partially-sectioned and enlarged view of a part of FIG. 1 relating to optical devices;

FIG. 3 is a schematic front view of the devices of FIG. 2;

FIG. 4 is an enlarged-scale view of a part of FIG. 1 relating to optical devices, and of the sample arranged on a rest base;

FIG. 5 is a schematic view from above of FIG. 2.

DESCRIPTION OF THE PREFERRED EMBODIMENTS

Figure 1:
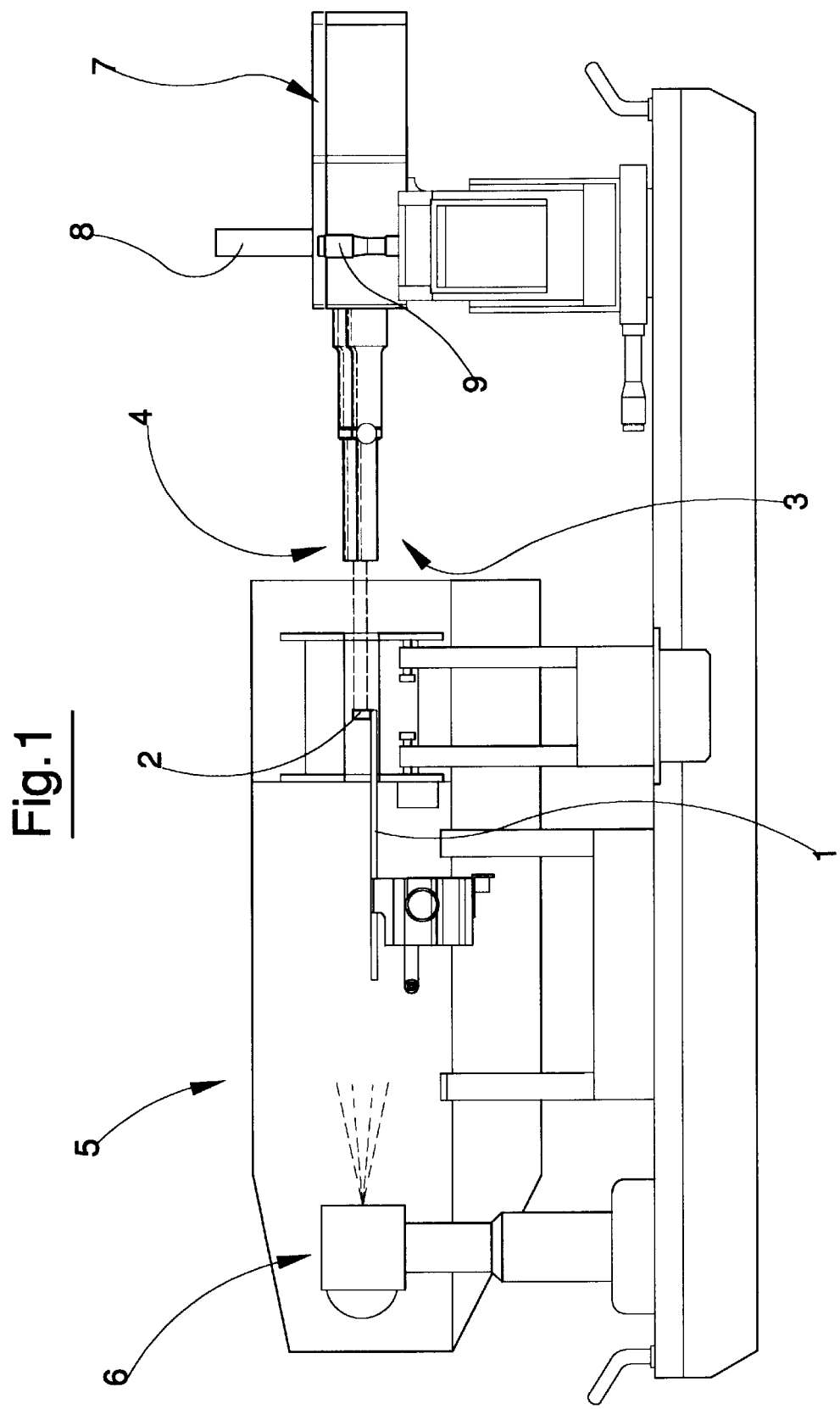
FIG. 1 is a schematic view in vertical elevation.

With reference to the figures of the drawings, 1 denotes a rest base for a sample 2 on which some dilatometric measurements are to be performed, i.e. a measurement (curve) of the dimensional variations induced on the sample when subjected to heating or cooling following a certain law.

The dilatometer further comprises two optical systems 3 and 4, identifying two optical paths located at a known predetermined reciprocal distance, and able to focus with predetermined magnification on the two ends of the sample 2 arranged on the rest base 1.

The optical systems 3 and 4 are arranged on planes which are parallel to the rest base 1 so that the first of the optical systems 3 can focus on one end of the sample, while the second of the optical systems 4 is focused on the other end thereof. More precisely, where the end of the sample is resting on the rest base, the optical system focuses on the line of contact between the rest base and the end of the sample.

The optical systems 3 and 4 are mechanically independent of one another and are able to move with respect to one another on parallel planes. For this purpose motors 8 and 9 of known type are provided, for example comprising a micrometric screw system moved by a step motor, for controlledly commanding a relative movement between the optical systems. In particular, it is possible to provide a motor only on the second optical system 4, which focuses on the terminal end of the sample, or on both optical systems 3 and 4.

The motor or motors can also cause movement of one or both of the optical systems, both on horizontal parallel planes (displacements in a vertical direction) and on vertical parallel planes (displacements in a horizontal direction), and on horizontal and vertical parallel planes (displacements in vertical and horizontal directions).

According to the above-described movements chosen, either one or two micrometric screw systems will be provided, combined with the optical system 4, and one only or two micrometric screw systems combined with the optical system 3. In the figures, and by way of example, only one micrometric screw system is combined to each optical system.

At least one monitoring and measuring device 7 is posteriorly associated to the two optical systems 3 and 4. The monitoring and measuring device 7 is above to gather focused images from the optical systems 3 and 4, which are arranged in such a way that the optical paths are arranged on planes which are parallel and perpendicular to the direction of a dilation that is to be measured. The monitoring and measuring device 7 is conformed in such a way as to receive both images taken by the independent optical systems 3 and 4. The rest base 1 and the sample 2 resting thereon are housed internally of a tubular oven 5, which is structured so as to place the sample 2 on the rest base 1 in perfect view of the optical systems 3 and 4, especially the end of the sample 2 which constitutes the dimension to be measured.

The sample 2 is illuminated by a light source 6 located in a diametrically opposite position to the optical systems 3 and 4, the base 1 being between the source and the optical systems 3 and 4. The source has the task of illuminating the sample 2 by contrast.

Like in known systems, the optical systems 3 and 4 comprise: a filter for infrared rays, to eliminate the infrared component emitted by the sample 2 when at a high temperature; a low-transmittance neutral filter to keep the contrast constant throughout the temperature range; a lens constituted by an achromatic duplet lens system having a long focal length, the task of which is to take the image of the inside of the oven and transfer it onto an enlarging device; a microscopic enlarging device which takes the image from the lens and transfers it (enlarged) to the monitoring and measuring device 7.

The monitoring and measuring device 7 can be a CCD interlaced sensor or a progressive scanning sensor, or any image digitizing system.

The invention can be used for measuring, along two perpendicular directions, dimensional variations induced on a sample by temperature variations, even where the variations occur over very large intervals.

To carry out the measurements, the sample 2 is positioned on the rest base 1 located internally of the oven 5 (the sample 2 must be illuminated and both ends should be visible from the outside); the two optical systems 3 and 4 are focused on the two ends of the sample 2 and, using the monitoring and measuring device 7, the images gathered by the optical systems 3 and 4 are read and the relative distance between the two images calculated; the effective distance between the two ends of the sample 2 is calculated on the basis of the relative distance between the two images and the distance between the two optical paths of the optical systems 3 and 4.

The sample 2 can be positioned vertically on the rest base 1 inside the tubular oven 5, or it can be arranged horizontally in a transversal direction.

The two optical systems 3 and 4 enable two optical paths to be defined, in ways that will be described in more detail herein below, which paths can focus the images of the ends of the sample 2 under examination. The enlarging of the image can be pushed to the limit of the optical resolution, focusing on only a few hundredths of a millimetre of the upper end of the sample 2 and the lower end thereof, resting on the rest base 1. As the enlarging factor is known, as is the distance between the two optic paths, the length of the sample can be calculated very precisely (to a resolution of 0.5 $\mu$m).

As mentioned herein above, with this new dilatometer the distance between the two optic paths can be varied, by actuating the motors according to needs and according to the conformation of the dilatometer, in both vertical and horizontal directions, while maintaining the optic paths on parallel planes. Supposing that it were decided to measure a dilation in a vertical direction (horizontal dilations are measured in the same way, with obvious differences): it is not necessary to actuate the motors as long as the variation is of limited entity, as the optical systems will be able to maintain sufficient resolution. The optical system 4 will be moved when the dilation of the sample 2 is great enough to exceed the resolution power of the optical system 4.

Obviously, in order to measure the dilation, it will be necessary to take account of the displacement effected, which in any case will simply be added to the measurements made by the monitoring and measuring device 7, inasmuch as the displacement occurs in the same direction as the dilation, and the optical paths are kept on parallel planes.

The motors used enable extremely precise displacements of the optical devices and in any case have error factors so low as to be uninfluential on the dilation measurements. The dilatometer functioning interval is considerably increased with no loss of precision.

In the dilatometer of the invention, differently to what happens in the previous dilatometer, the optical systems 3 and 4 are not solidly constrained one to another: the dilations of the rest base for the sample are not automatically compensated. Although the measures are dependent on the variations of the rest base for the sample, these variations are easily readable by the optical system 3 which focuses the lower end of the sample 2, so the variations can easily be eliminated from the measurement of the dilation of the sample by a simple algebraic sum, without the need for specific preliminary calibrations of the dilatometer. If the variations due to the rest base were of such an entity that they exceeded the resolution power of the optical system 3, the optic system 3 could be moved by the motor, so as to refocus the image on the end of the sample connected to the rest base. Obviously, in this case too, it will be necessary to take into account the displacement when evaluating the dilation. As stated above, the dilatometer can be provided with one motor only, associated to the second optical system 4, to increase the range of the dilatometer, and a further motor, associated to the first optical system 3, for increasing the temperature range of the dilatometer, which normally causes large variations in the dimensions of the rest base. The dilatometer can also be provided with two further means for moving the optical systems on parallel vertical planes (i.e. in a horizontal direction) in order to measure the transversal dilations of the sample 2.

All of these movements, which as has been mentioned occur while maintaining the optical paths on parallel planes, are exactly measurable and calculable, and influence the measurements taken in a linear direction. Thus they can easily be eliminated from the measurements taken by simple algebraic calculations (which can be done automatically).

What is claimed is:

1. An improved optical dilatometer, comprising a rest base for a sample to be examined, at least a first and a second optical systems, creating two optical paths located at a predetermined distance one from another and able to focus, with a predetermined enlargement, on two ends of the sample housed internally of an oven, which oven is structured so as to leave the sample visible to the at least a first and a second optical systems; further comprising at least a monitoring and measuring device able to gather images sent by the at least a first and a second optical systems; wherein: the at least a first and a second optical systems are mechanically independent of one another and are able to move with respect to one another on planes which are parallel to one another; a first motor is provided, of known type, for commandably causing a relative motion between the at least a first and a second optical systems.

2. The dilatometer of claim 1, wherein the optical paths are arranged on parallel planes which are perpendicular to a dilation to be measured.

3. The dilatometer of claim 1, wherein the first motor comprises at least one micrometric screw system, operated by a step motor, associated to one of the at least a first and a second optical systems and able to displace the one of the at least a first and a second optical systems in an exactly precise and definable way.

4. The dilatometer of claim 1, wherein the first motor comprises at least one micrometric screw system, operated by a step motor, associated to each of the at least a first and a second optical systems and able to displace each of the at least a first and a second optical systems in an exactly precise and definable way.

5. The dilatometer of claim 1, wherein the first motor comprises at least two micrometric screw systems, operated by a step motor, associated to each of the at least a first and a second optical systems and able to displace each of the at least a first and a second optical systems in an exactly precise and definable way along two directions, which directions are perpendicular one to another.

6. The dilatometer of claim 1, wherein each of the at least a first and a second optical systems comprises: a filter for infrared rays, for eliminating an infrared component emitted by the sample when the sample is at a high temperature; a low-transmittance neutral filter, for keeping a contrast constant throughout a temperature interval; a lens constituted by a duplet long-distance focusing achromatic lens for taking an image from inside the oven and transferring the image onto an enlarging device; a microscopic enlarging device, for taking the image from the lens and transferring it in an enlarged state onto a measuring device.

7. The dilatometer of claim 6, wherein the at least a monitoring and measuring device is constituted by an electronic visualizing device.

* * * * *